US00PP09197P

United States Patent [19]

Westerfield

[11] Patent Number: Plant 9,197

[45] Date of Patent: Jul. 11, 1995

[54] HILLARY'S SWEET LEMON' MINT

[76] Inventor: James E. Westerfield, 8059 Jefferson Rd., Freeburg, Ill. 62243

[21] Appl. No.: 141,069

[22] Filed: Oct. 26, 1993

[51] Int. Cl.[6] ..... A01H 5/00
[52] U.S. Cl. ..... Plt./100
[58] Field of Search ..... Plt. 100

[56] References Cited

U.S. PATENT DOCUMENTS

P.P. 2,908 7/1969 Murray ..... Plt./100
P.P. 8,645 3/1994 Sturtz ..... Plt./100

OTHER PUBLICATIONS

Huxley, A., et al., "*Mentha*" The New R.H.S. Dictionary of Horticulture 3, 1992 The Macmillan Press, Ltd. N.Y., pp. 220–221.

*Primary Examiner*—James R. Feyrer
*Attorney, Agent, or Firm*—Paul M. Denk

[57] ABSTRACT

A new and distinct hybrid of mint plant (Dulcia Citreus), the plant forms an attractive mound of leaves, and the stems of the plant tend to develop side-branching, with the tips of the stems providing multitudinous flowering of spaced clusters of lavender color blossoms, which gradually bloom outwardly towards the tip of each stem during their growing season; the leaves exhibit a dark green color, are heart shaped, and are typical labiatae, in opposing position.

2 Drawing Sheets

BACKGROUND OF THE INVENTION

This invention involves a nw member of the mint genus, which is an interspecific cross between *Mentha suaveolens*×*M. piperita.* The cultivation of mint plants has been long practiced with the use of mints for their culinary, antiseptic and aromatic qualities. For example, the wide and popular use of peppermint as a flavorful herb from which flavor principals can be extracted has led to the popular culture of this plant as a garden plant as well as industrially. Members of this genus are known by the gardner to offer a wide range of distinct tastes and aromas. Moreover, the known cross compatibility of species within this genus suggests that the range of characteristics of the genus can be even further expanded, through known breeding methods, to render further plants of unusual and valuable character. The plant of this invention represents such an improvement, and offers the gardener or grower a hardy new plant which is easily established and adapted to typical home garden conditions and which will find herbal uses as mentioned above.

SUMMARY OF THE INVENTION

The new plant of this invention is a mint plant which was created in a planned breeding program conducted by me in a controlled environment at The Westerfield House, in Freeburg, Ill., by the cross pollination of selected parent plants. The plant of this inveniton was a final selection attained from progeny resulting from the repeated crossing of 'Lime Mint', *Mentha piperita*×'Apple Mint', *M. suaveolens.*

The plant of this invention was achieved after repeated crosses performed during the flowering system in each of the years 1987–1990. Seeds resulting from the pollinations were collected and planted, and a population of widely diverse individuals resulted. The plant of this inveniton was conspicuously different from the remaining siblings of the noted cross due to its alluring fragrance and taste characteristics, and was selected for further observation and testing. With an appreciation that this plant was a good grower having excellent vigor, form and noteworthy growth characteristics, it was asecually reproduced by me by division of rhizomes at the same location. The clonal progeny of the plant have maintained the characteristics of the original selection through a series of asexual propogations and the plant has been determined to be stable.

Following selection, the plant was denominated 'Hillary's Sweet Lemon Mint'. This plant has been determined to be distinct and distinguished from each of its parent plants and from all other mint plants of which I am aware by the following combination of characteristics:

This plant produces a primary and normally two branches of floral spikes, or verticillasters, of thyrsi for, which taper to a pointed bud-forming terminal per main stem.

Basal mature nodal clusters of flowers are open and mature for pollination while those progressively toward the apex of the interrupted spike are progressively less mature. Mature flowers occur in verticils, are characterized by being male sterile, and have a soft lavender petal color, compared to the white petals with occasional slight pink blushes of the seed parent 'Apple Mint', and the purple petals with pink overtones coloration of the pollen parent 'Lime Mint'. The nodal clusters of flowers are normally subtended by two foliaceous bracts of opposite orientation.

This plant also as stems which are substantially rounder when compared with those of most members of the genus. The stems of this plant are not covered with coarse hair as characterizes the seed parent 'Apple Mint', but soft short hairs of very high density. Nor has this plant the red-colored stems of the pollen parent which also has a classic lime scent. Leaf and stem surfaces of 'Hillary's Sweet Lemon Mint' are finely and densely tomentose to a degree that they have a white to gray cast when moved in the light, and show a lighter red stem coloration when compared with the seed parent.

The aroma of this plant is soft, sweet lemon in character, and at least has the strength of the lime fragrance of the seed parent and the apple fragrance of the pollen parent. The physical appearance of flowering is nearly identical to that of the seed parent, 'Lime Mint', but has a lavender petal color rather than the purple color of 'Lime Mint'.

BRIEF DESCRIPTION OF THE VIEWS OF THE DRAWINGS

In reference to the drawing, the views of the drawing show the following characterstics of the plant of this invention:

The First Sheet of drawing is a close-up, essentially side perspective view, of the plant in full bloom stage and which depicts the floral habit of this plant in varying stages; the leaves of the plant with the venation, kmargin characteristics and fine surface tomentum; the stems of the plant showing the shape of the stems; and the branch breaking action of the plant at the flowering stage; and The Second Sheet of drawing, in the top photograph, depicts rooted cutting initiates of the plant in nursery containers from top view, and shows the form and density of plantlets in an early stage of growth which is suitable for transplanting. The bottom photograph shows mature leaves with the two specimens on the left having the top surfaces exposed, and those on the right having the bottom surfaces exposed, as well as a dime to reflect the relative size of the mature leaves. These photographs show the color of the leaves reasonably accurately.

The color values to follow were defined by reference to specific color values presented in *The Royal Horticultural Society Colour Chart* prepared in association with the Flower Council of Holland, Leiden, 1992. Ordinary color descriptions are also presented where appropriate.

The Physical Description of Parent Plants and Offspring:

*Menta suaveolens 'Apple Mint'*.—Large soft hairy, light green leaves giving off a slight sweet apple scent. The flower is white with occasional slight overtone of pink.

*Mentha piperita 'Lime Mint'*.—A red-stemmed Mint with deep green, smooth medium sized leaves, giving off a true, lime scent. Its flowers are purple with pink overtones.

*Offspring.—Mentha dulcia* Citreus 'Hillary's Sweet Lemon Mint'. Its leaves are deep green, with grey overtones. This grey characterstic is due to slight hairy surface growth on leaves, which is a reflection of its Parent, Apple Mint. It has a slight, red-stemmed characteristic, reflecting its other parent, Lime Mint. The scent/aroma of its leaf is soft, sweet Lemon, which can be interpreted as a reflection of the citrus scent/aroma within its parent, Lime Mint. The physical appearance of its flowering characteristic is identical to its parent Apple Mint, excepting its flowers are true purple.

DETAILED DESCRIPTION

Botanical classification: Mentha Dulcia Citreus . . . Hillary's Sweet Lemon Mint.

Parentage: Apple Mint (*Mentha suaveolens*); Lime Mint (*Mentha piperita*).

PLANT DESCRIPTION

Form: Grows upright, approximately 24 inches tall with unusual heavy side branching, thus giving a mounding effect.

Growth habit: Very strong in its rate of growth with rhizomes (runners) forming in its early life cycle.

Foliage description: Leaves are typical Labiatae, in opposing each other on square stems. The heart shaped leaves retain their firmness and succulence in sun or deep shade. In their mature size/stage the leaves are two inches long, by one and a half inches wide 50 mm long, by 37 mm wide. The true sweet lemon scent /aroma from the leasves is present in its newly forming stage and accelerates, reaching its peak of fragrance in their mature stage of growth. Since leaf tomentum is very soft, the top and bottom surface texture of this Hydrid is smooth to the touch. When eaten, is lightyly course to the tongue. The tomentum o the leaves resembles until close examination, very fine dust. The sheer density of the leaf hairs on both top and bottom of leaf can only be described in this way. Their attitude is toward the leaf tip. They are 0.80 mm.

*Leaf color.*—The leaves, whether they be newly forming, or the final mature size, remain a constant deep green. Color Chart: FAN 3 138-A. The stems, the leaf midrib and venation, when viewed from the bottom of the leaf, are a lighter shade of green. Color Chart: FAN 3 139-C. The midrib and venation, when viewed from the bottom of the leaf, are pronounced, standing above the surface 1.6 mm.

*Leaf thickness.* 0.80 mm. The internode length of the Hybrid is 100–125 mm, resulting in very dense foliage. In comparison to Parent plant, the internode length of the male Parent is 150–175 mm. The internode length of seed Parent is 125–150 mm.

Flowering description:

*Flowering color.*—The flower color of the male Parent Apple Mint (Suaveolens) is white, with occasional very light pink overtones. The flower color of the seed Parent Lime Mint (Piperita) can only be described as pinkish purple. Upon initial flower the flowers of the Hybrid are true purple: Color Chart: FAN 2 PURPLE GROUP 76-A Within 4–5 days, this initial color slowly fades to pinkish purple, identical to initial color of seed parent flower: Color Chart: FAN 2 VIOLET GROUP 84-C.

*Flowering habit.*—In appearance, the description of its physical form and flowering habit is identical to the male parent. The Hybrid forms a bracketed, elongated, coneshaped spear of flowers approximately 125–150 mm long. There are 10 flower clusters per spear. There are approximately 30 flowers per cluster. The distance between bracketed flower clusters is approximately 12 mm. Two flowering side spears form below the base of the flower cone 50 mm from said base. Thus the distance from base of side spears to tip of flower cone when matured is approximately 150 mm. Since each main branch produces heavy side branching, it is thus highly floriferous. The flowering habit of the Hybrid is fairly typical of members of the sAge Family in general, and of the Mint genus specifically.

*Natural flowering season.*—The Hybrid blooms the exact same time period as both parent plants, which is August through mid-October.

ESSENTIAL OIL REPORT

On Sep. 19, 1994, Professor Arthur O. Tucker, Research Professor for the Delaware State University, of Dover, Del., forwarded the following Essential Oil Study on Mentha 'Hillary's Sweet Lemon'.

ESSENTIAL OIL REPORT ON MENTHA 'HILLARY's SWEET LEMON'

"This essential oil report on Mentha 'Hillary's Sweet Lemon', is the result of three distillations and GC/MS analysis. Principal components, or those over 10% are indicated in bold:

| Compound | Mean + one Standard Deviation % |
|---|---|
| a-pinene | 1.96 ± 1.30 |
| β-pinene | 1.07 + 0.37 |
| sabinene | 3.02 ± 1.10 |
| myrcene | 1.89 ± 0.69 |
| LIMONENE | 11.29 ± 2.39 |
| 1.8-cineole | 3.20 ± 0.21 |
| (E)-B-ocimene | 3.32 ± 0.77 |
| p-cymene | 0.80 ± 0.95 |
| iso-amyl isovalerate | 0.95 ± 0.13 |
| allo-ocimene | 0.16 ± 0.04 |
| menthone | 0.04 ± 0.01 |
| β-bourbonene | 0.03 ± 0.02 |
| linalool | 0.33 ± 0.13 |
| β-caryophyllene | 0.32 ± 0.02 |
| CIS-CIHYDROCARVONE | 24.84 ± 2.39 |
| trans-dihydrocarvone | 3.52 ± 0.34 |
| DIHYDROCARVEYL ACETATE | 11.52 ± 1.43 |
| a-humulene | 0.23 ± 0.06 |
| neodihydrocarveol | 7.05 ± 0.60 |
| germacrene D | 3.32 ± 0.85 |
| CARVONE | 12.29 ± 3.02 |
| δ-cadinene | 0.05 ± 0.08 |
| cis-carveyl acetate | 0.59 ± 0.11 |
| isodihydrocarveol | 0.12 ± 0.01 |
| dihydrocarveol | 0.09 ± 0.02 |
| trans-carveol | 0.09 ± 0.02 |

-continued

| Compound | Mean + one Standard Deviation % |
|---|---|
| cis-carveol | 0.15 ± 0.03 |
| cis-jasmone | 0.28 ± 0.04 |
| caryophyllene oxide | 0.08 ± 0.07 |
| elemol | 2.31 ± 0.20 |
| viridifloral | 0.70 ± 0.09 |
| thymol | 0.53 ± 0.07 |
| a-eudesmol | 0.10 ± 0.02 |
| β-eudesmol | 0.12 ± 0.02 |

The oil yield was 0.06±0.01%. The essential oil of Mentha 'Hillary's Sweet Lemon' is not unusual in either its chemical compounds or the combination thereof. However, while the OIL has no market value, no clone of Mentha, that is this HIGH In cis-dihydrocarvone is currently in the herb PLANT trade, and Mentha 'Hillary's Sweet Lemon' would add a different nuance to cooking. No deleterious substances were found in the essential oil to prevent its consumption. Any "lemon" odor would come from the limonene, since the other major components smell of spearmint.

I claim:

1. A new and distinct variety of mint plant (Dulcia Citreus) named Hillary's Sweet Lemon Mint, characterized by the following combination of characteristics:

(a) forms a bushy plant in proximity with the ground and extends rather mounded upwardly in its formation, (b) exhibits strong growth habit, (c) has elongated stems that develop side-branching, (d) and which flowers along the tip of the stem into a cone-shape formation, with the flowers being multitudinous, and arranged in clusters, upwardly along the length of the stem, and gradually blooming outwardly towards the tip of the stem, and (e) exhibits good sustaining qualities throughout flowering, substantially as shown and described.

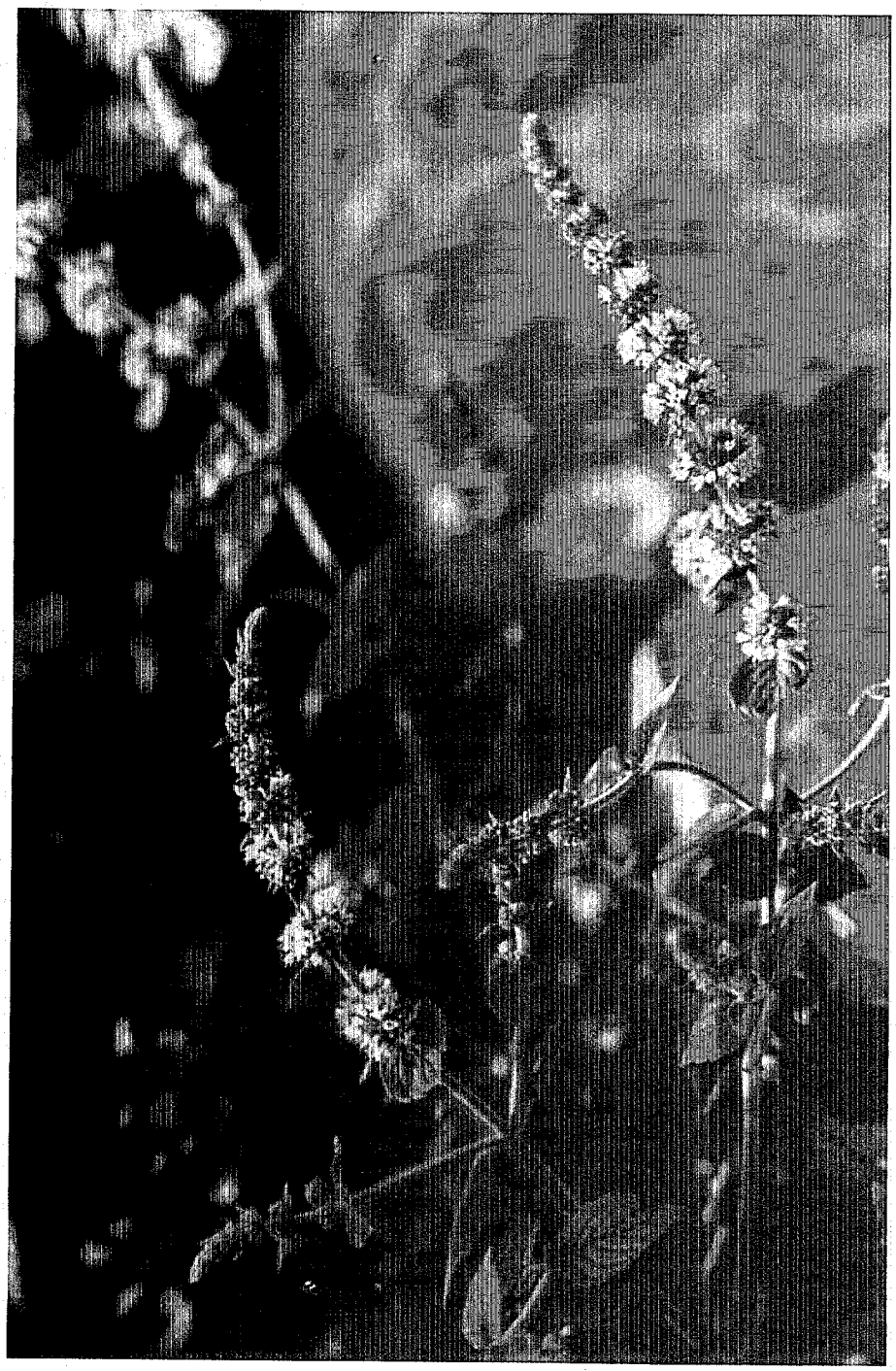

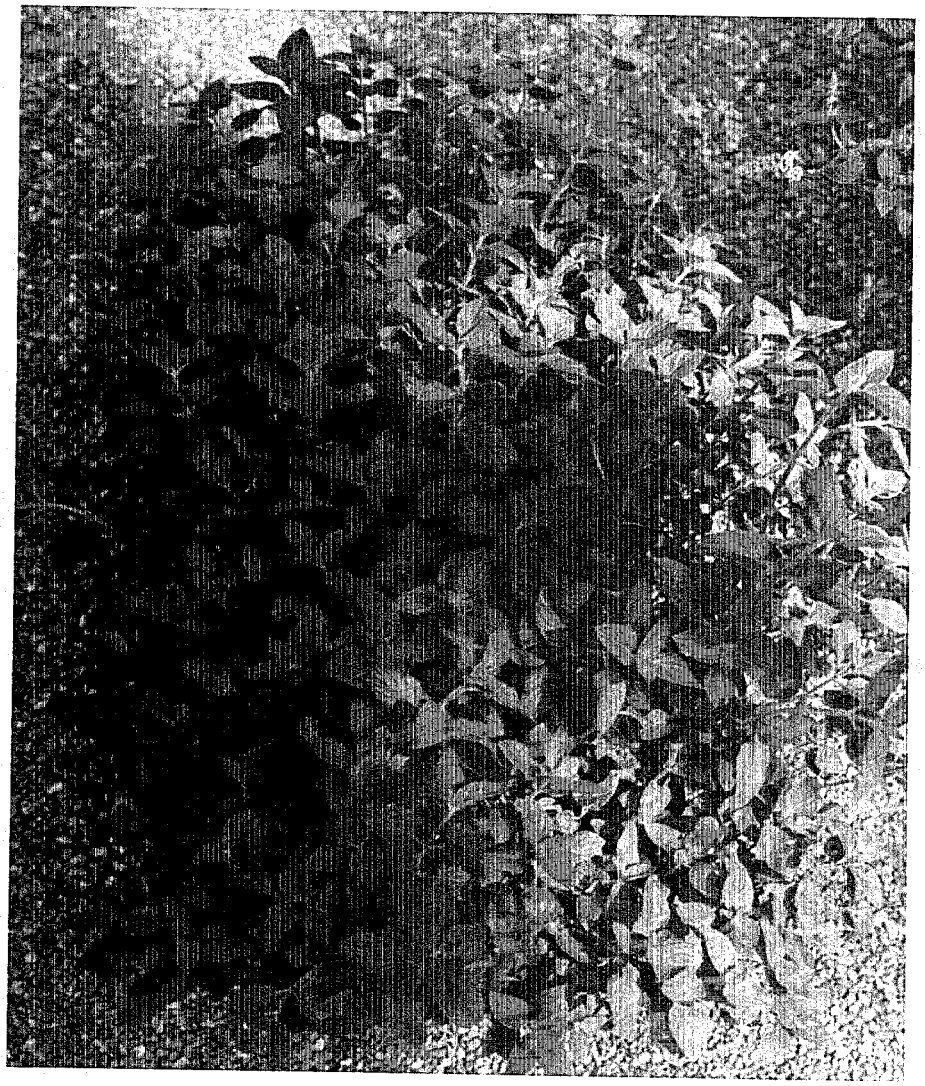
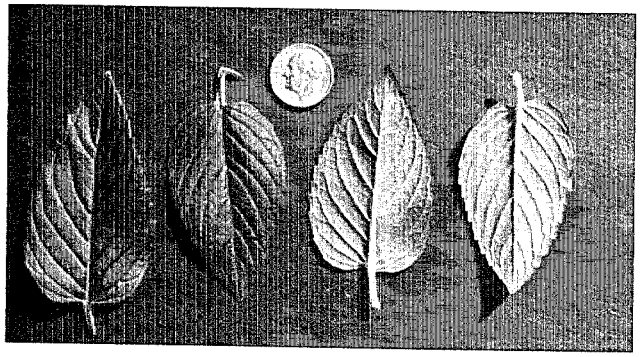

* * * * *